(12) United States Patent
Lai

(10) Patent No.: US 9,144,623 B2
(45) Date of Patent: Sep. 29, 2015

(54) REFRIGERATOR WITH PLASMA DEVICE

(71) Applicant: Chung-Ping Lai, Shin Jwu Hsien (TW)

(72) Inventor: Chung-Ping Lai, Shin Jwu Hsien (TW)

(*) Notice: Subject to any disclaimer, the term of this patent is extended or adjusted under 35 U.S.C. 154(b) by 170 days.

(21) Appl. No.: 14/072,797

(22) Filed: Nov. 6, 2013

(65) Prior Publication Data

US 2015/0121937 A1   May 7, 2015

(51) Int. Cl.
*F25D 11/00*   (2006.01)
*A61L 9/22*   (2006.01)
*F25D 17/06*   (2006.01)
*F25D 17/04*   (2006.01)

(52) U.S. Cl.
CPC .............. *A61L 9/22* (2013.01); *F25D 17/042* (2013.01); *F25D 2317/041* (2013.01)

(58) Field of Classification Search
CPC . F25D 11/00; F25D 17/062; F25D 2317/041; A61L 19/22
USPC ........................................... 62/314, 414, 419
See application file for complete search history.

(56) References Cited

U.S. PATENT DOCUMENTS

| | | | | | |
|---|---|---|---|---|---|
| 3,596,128 | A | * | 7/1971 | Elliott | 313/231.61 |
| 5,593,517 | A | * | 1/1997 | Saito et al. | 148/301 |
| 5,927,100 | A | * | 7/1999 | Persson | 62/356 |
| 6,248,998 | B1 | * | 6/2001 | Okumoto et al. | 250/288 |
| 6,322,756 | B1 | * | 11/2001 | Arno et al. | 422/171 |
| 2001/0001284 | A1 | * | 5/2001 | Shaw et al. | 428/216 |
| 2001/0033901 | A1 | * | 10/2001 | Affinito | 427/569 |
| 2007/0157646 | A1 | * | 7/2007 | Kim et al. | 62/187 |
| 2008/0155985 | A1 | * | 7/2008 | Labrador | 60/698 |
| 2008/0187728 | A1 | * | 8/2008 | Borowiec et al. | 428/203 |
| 2009/0196801 | A1 | * | 8/2009 | Mills | 422/186 |
| 2009/0226530 | A1 | * | 9/2009 | Lassner et al. | 424/497 |
| 2013/0098075 | A1 | * | 4/2013 | Hegedus et al. | 62/80 |

* cited by examiner

*Primary Examiner* — Mohammad M Ali
(74) *Attorney, Agent, or Firm* — Alan D. Kamrath; Kamrath IP Lawfirm, P.A.

(57) ABSTRACT

The refrigerator includes a thermally insulated box with a first board, a plasma device and a pipeline, all of which are embedded in the first board. The plasma device includes an atomizer with a water tank and a first fan, a plasma generator and a pipeline. The plasma generator is hermetically connected to the atomizer and has an electrode device. The electrode device includes a dielectric plate and a plurality of electrode rods embedded therein. The electrode rods are interlacedly electrically connected to an AC source. The pipeline is hermetically connected to the plasma generator and composed of an inlet section with an inlet, an outlet section with at least one outlet and a middle section communicating with the dielectric plate. The inlet is provided with a second fan.

9 Claims, 4 Drawing Sheets

REFRIGERATOR WITH PLASMA DEVICE

BACKGROUND OF THE INVENTION

1. Technical Field

The invention relates to plasma generation, particularly to plasma generators built in refrigerators.

2. Related Art

Refrigerators are a necessary appliance in daily life. A refrigerator is a hodgepodge of all kinds of fresh foods, so it is always full of odor and bacteria. Thus, many refrigerators are equipped with a deodorizer and/or sterilizer, such as silver ion, ultraviolet (UV), ozone, enzyme or negative ion. All these deodorizers and sterilizers are under the reach of plasma in performance. On the other hand, vegetables and fruit will produce ethylene during storage in a refrigerator. Ethylene is a gaseous plant hormone, which can regulate or affect the physiological process of growth and development of plants. As a result, effectively reducing production of ethylene can defer fruit's maturation. Plasma possesses a great effect in decomposition and reduction of ethylene.

Plasma is a gas which is dissociated into positive and negative particles in an electromagnetic field. Plasma contains negative and positive ions, electrons, free radical and neutral particles. In an electric field, electrons are much larger than positive ions in mean free path, so electrons can be intensively accelerated to carry high energy (10 or more eV). Such high-energy electrons colliding with atoms or molecules can break chemical bonds in a molecule to form reactive free radical or to ionize the atoms and molecules. The ionized electrons will be further accelerated to make other collisions and to form more electrons, ions and free radicals (called "chain reaction"). Finally, plasma with high-energy electrons and highly-reactive free radicals is produced. U.S. Pat. Nos. 3,212,974, 4,275,287 and 4,778,561 disclose methods for producing plasma.

In an electric field, electrons in plasma are much easier to absorb energy than ions. Thus temperature of the electrons in plasma can reach up to hundreds of thousands of centigrade and that of the other particles is about room temperature. Because high-temperatured electrons are high reactive and can easily break bonds, plasma can be obtained at room temperature.

It is the most effective and economical manner to produce plasma at 1 atm. In order to stably produce plasma, the system must operate at low pressure. Thus a vacuum chamber and vacuum pump are needed to keep a low pressure circumstance. This will increase costs of manufacturing and maintenance and decrease the amount of production in a unit time. For example, a vacuum pump is easy to be damaged by particles and corrosion. A vacuum pump is not needed if plasma is produced at normal atmospheric pressure. Atmospheric pressure plasma technology can simplify manufacturing costs and process. As a result, atmospheric pressure plasma technology can extensively extend application of plasma.

Electrons in low pressure plasma are much longer than other particles in mean free path, so it can obtain more energy enough to ionize other gases. When the pressure is 1 atm., however, gaseous molecules collide frequently and the mean free path is so short. It is hard that electrons obtain enough energy to ionize gaseous molecules. As a result, plasma cannot be produced.

At this time, there are two methods for producing plasma: (1) increasing the voltage of the external power source to thousands of volts to add energy to electrons; and (2) providing a large amount of current to heat up the gaseous molecules to form high temperature plasma.

Additionally, in comparison with low pressure plasma, atmospheric pressure plasma may meet a problem of unstable discharge, i.e., plasma often appears at certain local areas. Thus, expensive cyanide gas or helium must be used to serve as an activator.

Because of the above problems, plasma being applied in refrigerators is still difficult in technology. Atmospheric pressure plasma with low cost and high efficiency is an issue to be solved by the industry.

SUMMARY OF THE INVENTION

An object of the invention is to provide a refrigerator with a plasma device, which can produce plasma under atmospheric pressure. This can provide refrigerators better effect of deodorization and sterilization, dissociate ethylene from vegetables and fruit, and defer fruit's maturation.

To accomplish the above object, the refrigerator of the invention includes a thermally insulated box with a first board, a plasma device and a pipeline, all of which are embedded in the first board. The plasma device includes an atomizer with a water tank and a first fan, a plasma generator and a pipeline. The plasma generator is hermetically connected to the atomizer and has an electrode device. The electrode device includes a dielectric plate and a plurality of electrode rods embedded therein. The electrode rods are interlacedly electrically connected to an AC source. The pipeline is hermetically connected to the plasma generator and composed of an inlet section with an inlet, an outlet section with at least one outlet and a middle section communicating with the dielectric plate. The inlet is provided with a second fan.

DETAILED DESCRIPTION OF THE INVENTION

Figure 1:
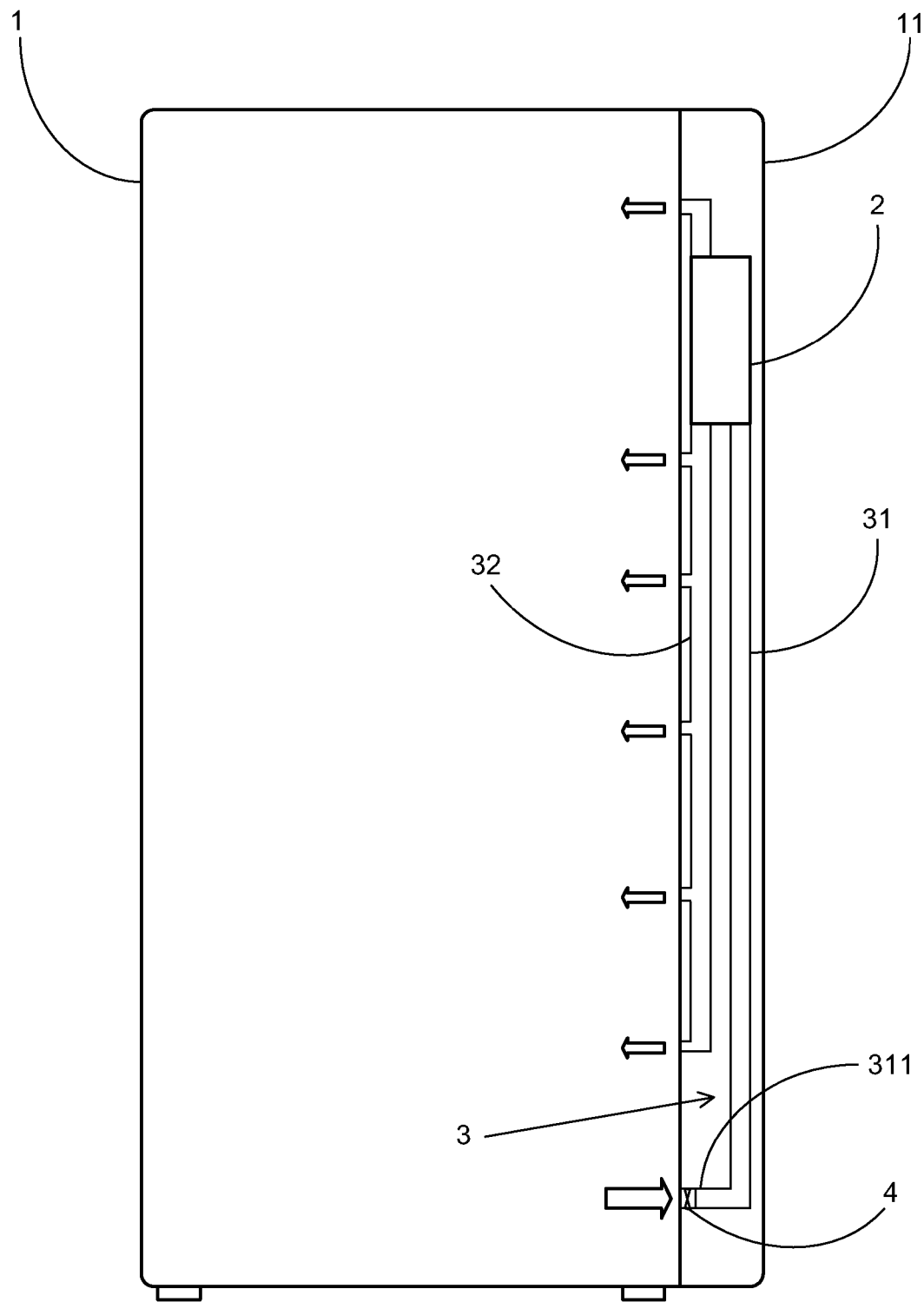
FIG. 1 is a schematic view showing the arrangement of the invention.

Please refer to FIG. 1. The invention provides a refrigerator with a plasma device. The refrigerator shown in FIG. 1 is of an upright type for home use. The refrigerator has a thermally insulated box 1 composed of a plurality of boards. A plasma device 2 is embedded in a first board 11 of the boards. In the shown embodiment, the first board 11 is, but not limited to, a door. Any other board can be used to embed the plasma device 2. A middle section of a pipeline 3 is hermetically connected to the plasma device 2. The rest of the pipeline 3 other than the middle section form an inlet section 31 and an outlet section 32. An inlet 311 of the inlet section 31 is disposed with a second fan 4 for introducing air into the pipeline 3 through the inlet 311. The air in the inlet section 31 will pass the plasma device 2 and flow out from the outlet section 32.

Figure 2:
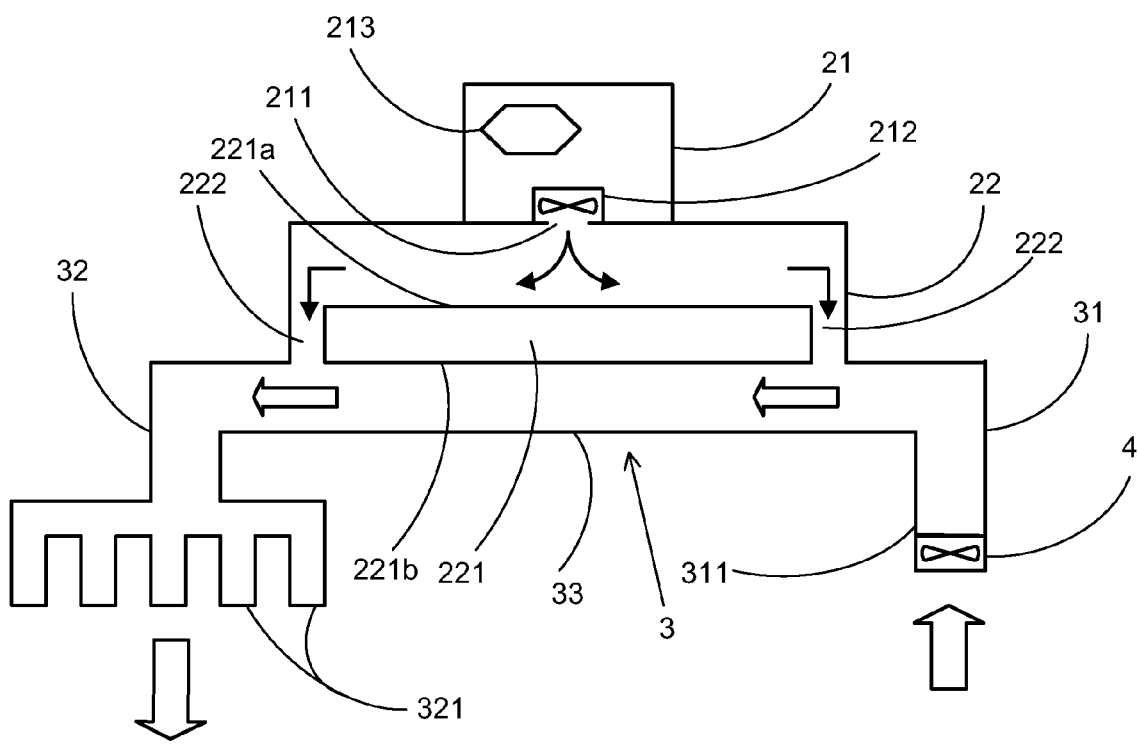
FIG. 2 is a schematic view of the plasma device of the invention.

Please refer to FIG. 2. The plasma device 2 is primarily composed of an atomizer 21 and a plasma generator 22. The atomizer 21 includes a water tank 213 and a first fan 212 for blowing mist from the water in the water tank 213. The plasma generator 22 is hermetically connected to the atomizer 21 and is provided with an aperture 211 on the first fan 212 for blowing mist into the plasma generator 22.

The plasma generator 22 includes an electrode device 221 which has a first side 221a facing the first fan 212 and a second side 221b opposite to the first side 221a. Plasma will be produced over the second side 221b. The electrode device 221 is located in the middle section 33 of the pipeline 3, and the air in the pipeline 3 just passes the second side 221b of the electrode device 221. The electrode device 221 is suspendedly fixed in the plasma generator 22, so a passage 222 is formed beside the electrode device 221 for allowing the mist from the atomizer 21 to enter the pipeline 3. The mist can make an effect of heat dissipation to the electrode device 221 when it is flowing.

The second fan 4 at the inlet 311 of the pipeline 3 can push the air in the pipeline 3 to flow. The outlet section 32 of the pipeline 3 is provided with a plurality of outlets 321. Of course, a single outlet 321 is available. The air with plasma and mist can flow out from the outlets 321 to enter the inside of the refrigerator.

Figure 3:
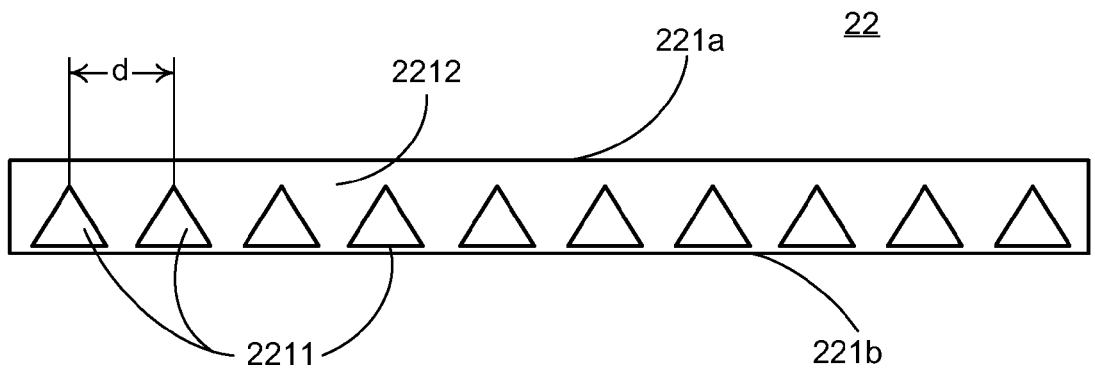
FIG. 3 is a side view of the dielectric plate of the invention.
Figure 4:
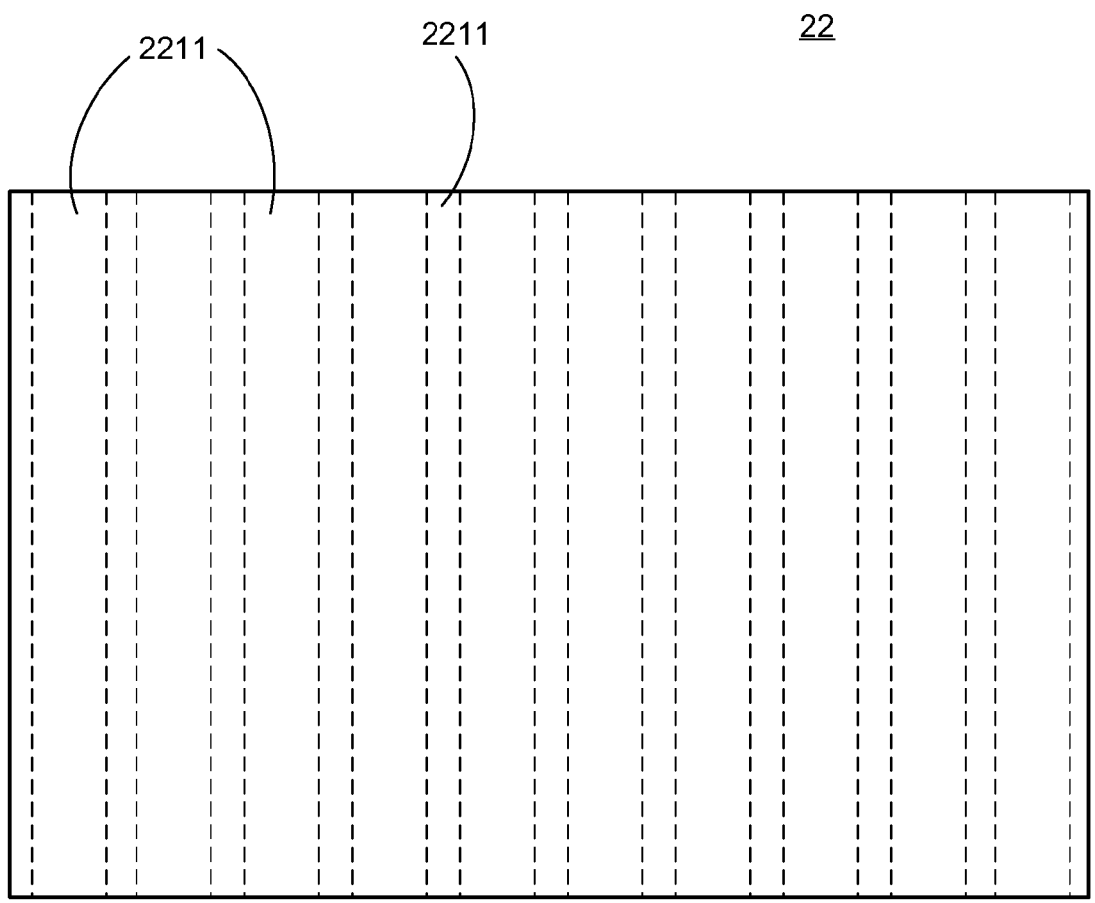
FIG. 4 is a top view of the dielectric plate of the invention.

Please refer to FIGS. 3 and 4. The electrode device 221 is composed of a dielectric plate 2212 and a plurality of electrode rods 2211 embedded in the dielectric plate 2212. The electrode rods 2211 are parallelly arranged at regular intervals. The dielectric plate 2212 may be made of a ceramic or glass material. The distance d between two adjacent electrode rods 2211 is between 0.05 mm and 5 mm. The cross section of the electrode rod 2211 is triangular or any other shapes. Additionally, the electrode rods 2211 are nearer to the second side 221b of the dielectric plate 2212 than the first side 221a to form a stronger electric field over the second side 221b. This will make plasma generated overt the second side 221b. It is noted that a byproduct of ozone will be produced when generating plasma. Ozone can help to dissociate chemical residues.

Figure 5:
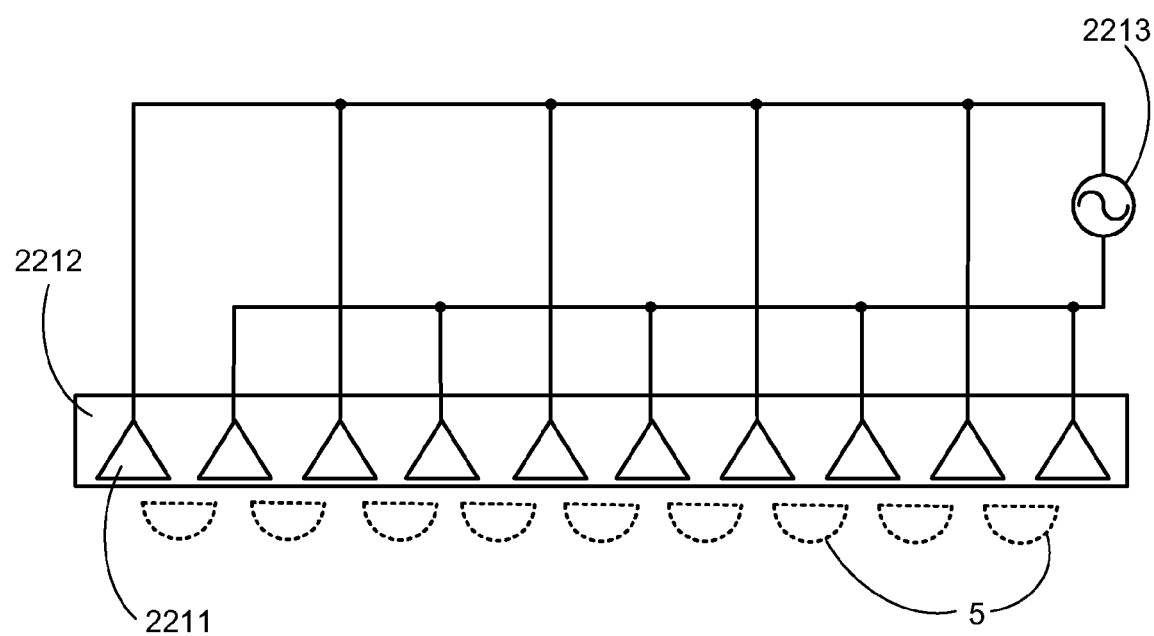
FIG. 5 is a schematic view showing the wiring of the electrode rods and the production of plasma.

As shown in FIG. 5, the electrode rods 2211 are interlacedly electrically connected two terminals of an alternating current (AC) power source 2213. In other words, two adjacent electrode rods 2211 are opposite in electric polarity. The frequency range and voltage range of the AC power source 2213 may be from 50 Hz to 1 MHz and from 100 V to 100 KV, respectively. The strongest electric fields are located the areas between two adjacent electrode rods 2211 over the second side 221b. Air molecules passing these areas will be ionized into plasma. The semicircular areas pointed by reference number 5 just express the generation of plasma.

Preferably, the atomizer 21 may be further provided with a switch to control power on/off. When the atomizer 21 is shutdown, the concentration of ozone becomes high because of no dilution by mist so as to cause a strong effect of dissociating chemical residues. While when the atomizer 21 is activated, the concentration of ozone becomes low and the proportion of plasma becomes high because of dilution by mist so as to cause a fresh smell to the user as forest bathing.

It will be appreciated by persons skilled in the art that the above embodiment has been described by way of example only and not in any limitative sense, and that various alterations and modifications are possible without departure from the scope of the invention as defined by the appended claims.

What is claimed is:

1. A refrigerator comprising:
    a thermally insulated box, composed of a plurality of boards including a first board; and
    a plasma device, embedded in the first board, comprising:
        an atomizer, having a water tank and a first fan for blowing mist;
        a plasma generator, hermetically connected to the atomizer, being provided with an aperture on the first fan for introducing mist from the atomizer, having an electrode device, wherein the electrode device comprises a dielectric plate and a plurality of electrode rods embedded therein, the electrode rods are parallelly arranged at regular intervals and interlacedly electrically connected to two terminals of an alternating current (AC) power source, the dielectric plate has a first side facing the first fan and a second side opposite to the first side, and plasma is generated over the second side; and
        a pipeline, embedded in the first board, hermetically connected to the plasma generator, composed of an inlet section with an inlet, an outlet section with at least one outlet and a middle section communicating with the second side of the dielectric plate, and the inlet being provided with a second fan.

2. The refrigerator of claim 1, wherein a distance between two adjacent electrode rods is between 0.05 mm and 5 mm.

3. The refrigerator of claim 1, wherein a frequency range of the AC power source is from 50 Hz to 1 MHz.

4. The refrigerator of claim 1, wherein a voltage range of the AC power source is from 100 V to 100 KV.

5. The refrigerator of claim 1, wherein the electrode rods are nearer to the second side of the dielectric plate than the first side.

6. The refrigerator of claim 1, wherein a cross section of the electrode rod is triangular.

7. The refrigerator of claim 1, wherein the dielectric plate is made of a ceramic material.

8. The refrigerator of claim 1, wherein the dielectric plate is made of a glass material.

9. The refrigerator of claim 1, wherein the electrode device is suspendedly fixed in the plasma generator, a passage is formed beside the electrode device for allowing mist from the atomizer to enter the pipeline.

* * * * *